US012702286B2

(12) United States Patent
Inglis et al.

(10) Patent No.: US 12,702,286 B2
(45) Date of Patent: Aug. 11, 2026

(54) AUTOMATIC STEERING OF AN INTRODUCER WITH A VIDEO LARYNGOSCOPE

(71) Applicant: Covidien LP, Mansfield, MA (US)

(72) Inventors: Peter D.C. Inglis, Boulder, CO (US); Derek S. Tata, Longmont, CO (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 18/600,251

(22) Filed: Mar. 8, 2024

(65) Prior Publication Data

US 2024/0324869 A1 Oct. 3, 2024

Related U.S. Application Data

(60) Provisional application No. 63/492,912, filed on Mar. 29, 2023.

(51) Int. Cl.
*A61B 1/267* (2006.01)
*A61B 1/00* (2006.01)
*A61B 1/005* (2006.01)
*A61B 1/05* (2006.01)

(52) U.S. Cl.
CPC .......... *A61B 1/267* (2013.01); *A61B 1/00006* (2013.01); *A61B 1/000096* (2022.02); *A61B 1/00045* (2013.01); *A61B 1/00066* (2013.01); *A61B 1/0051* (2013.01); *A61B 1/05* (2013.01)

(58) Field of Classification Search
None
See application file for complete search history.

(56) References Cited

U.S. PATENT DOCUMENTS 11,147,634 B1 * 10/2021 Nekhendzy ........ A61B 1/00133
2020/0254204 A1 8/2020 Moffat et al.
2021/0361895 A1 * 11/2021 Nekhendzy ........ A61B 1/00009
2022/0044791 A1 2/2022 Holmstrom
2023/0149135 A1 * 5/2023 Lipnik ................ A61C 9/0053 433/214
2025/0221615 A1 * 7/2025 Chauhan .............. A61B 1/0051
2025/0281022 A1 * 9/2025 Okuno ............... A61B 1/00009
2025/0288186 A1 * 9/2025 Mino ..................... A61B 10/04

FOREIGN PATENT DOCUMENTS

WO 2021/236677 A1 11/2021
WO 2021/245695 A1 12/2021
WO 2022/133248 A1 6/2022
WO 2022/266500 A1 12/2022

OTHER PUBLICATIONS

International Search Report for International Application No. PCT/IB20204/052724 mailed Jun. 18, 2024 (12 pages).

* cited by examiner

*Primary Examiner* — Tessa M Matthews

(57) ABSTRACT

Methods and systems for automatic steering of a blind introducer based on images from an independent camera (e.g., a camera of a video laryngoscope) are disclosed. A real time image of a video laryngoscope may be analyzed by a trained ML model to output a classification for the image. The classification may be associated with steering instructions for an introducer. The steering instructions may be provided to the introducer to cause steering of a distal end of the introducer in real time. The trained ML model may be generated by AI or ML training algorithms, based on multiple sets of multiple still-shot training images associated with a finite quantity of classifications.

20 Claims, 11 Drawing Sheets

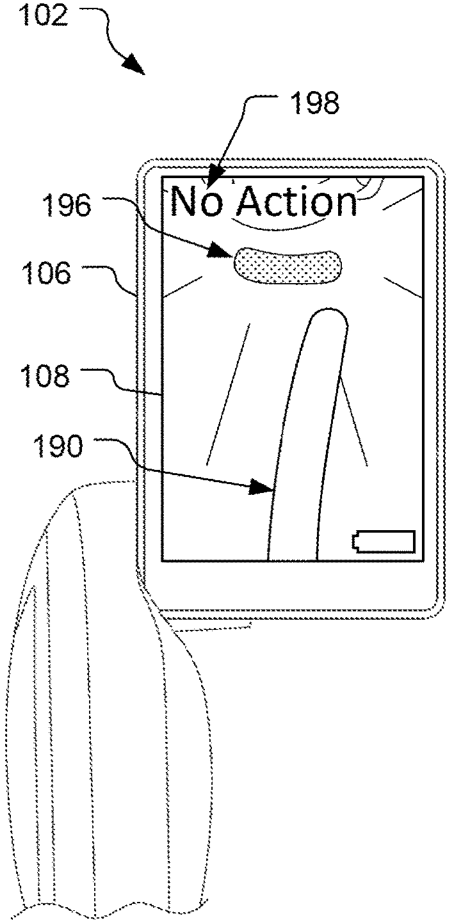
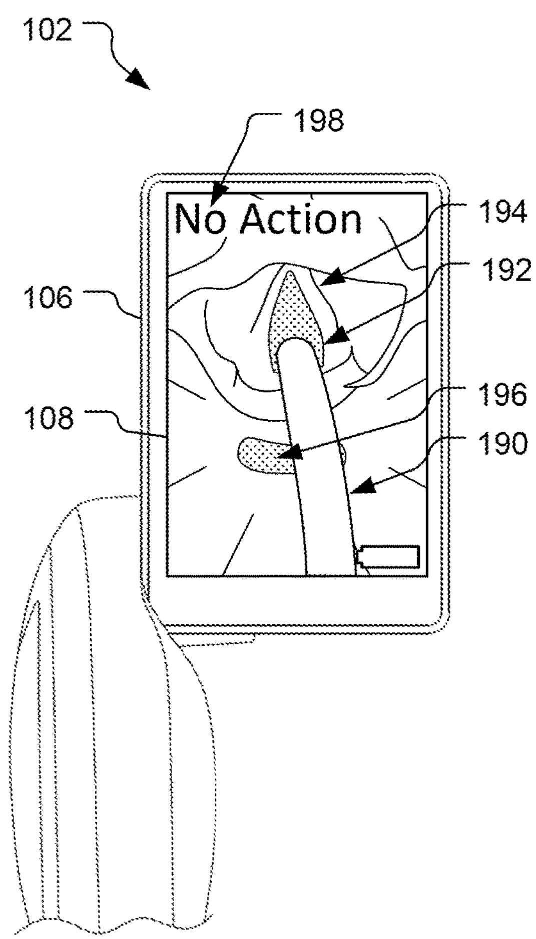
FIG. 5E
FIG. 5F

AUTOMATIC STEERING OF AN INTRODUCER WITH A VIDEO LARYNGOSCOPE

CROSS-REFERENCE TO RELATED APPLICATIONS

This application claims the benefit of U.S. Provisional Application No. 63/492,912 filed Mar. 29, 2023, titled "Automatic Steering of an Introducer with a Video Laryngoscope," which is incorporated herein by reference in its entirety.

INTRODUCTION

Laryngoscopes are commonly used during intubation of a patient (e.g., an insertion of an endotracheal tube into a trachea of the patient). In video laryngoscopy, a medical professional (e.g., a doctor, therapist, nurse, clinician, or other practitioner) views a real-time video feed, captured via a camera of the video laryngoscope, of the patient's larynx on a display screen to facilitate navigation and insertion of tracheal tubes within the airway.

A tracheal tube introducer, otherwise called a bougie, is a long, flexible instrument that may be used to assist in placing an endotracheal tube into a patient's trachea during an intubation. Introducers may aid a physician with intubations in difficult airway environments. Some introducers may have a tip, or distal end, which is steerable. For example, the distal end may be actively controllable to bend, turn, rotate, or otherwise move the distal end in a desired direction, such as to navigate through or towards anatomy of the patient. The introducer itself may not have a camera or other visualization component (e.g., the introducer may be blind).

It is with respect to this general technical environment that aspects of the present technology disclosed herein have been contemplated. Furthermore, although a general environment is discussed, it should be understood that the examples described herein should not be limited to the general environment identified herein.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an aspect, a method for steering an introducer with a video laryngoscope is disclosed. The method includes receiving an image from a camera of a video laryngoscope, the image including a distal end of an introducer and an anatomical structure. The method further includes providing the image as an input to a trained machine-learning (ML) model and receiving as output from the trained ML model, a classification of the image. Based on the classification, the method further includes generating a steering instruction for the introducer. Additionally, the method includes causing the distal end of the introducer to be steered in accordance with the steering instruction.

In an example, the method further includes training the trained (ML) model to classify images as steering instructions for the blind introducer, wherein the trained ML model is trained using a training dataset including a first set of training images pre-classified with a first steering instruction and a second set of training images pre-classified with a second steering instruction. In another example, the method further includes receiving an indication to automatically steer the introducer, wherein generating the steering instruction for the introducer is in response to the indication to automatically steer the introducer. In a further example, the anatomical structure is a trachea or vocal cords. In yet another example, the method further includes displaying, at the video laryngoscope, a visual indicator associated with the steering instruction. In still a further example, the classification includes the steering instruction and wherein the steering instruction includes a direction and a magnitude for steering the distal end. In another example, the classification of the single frame is selected from a finite set of at least four classifications. In a further example, the image is from a video feed of the camera of the video laryngoscope. In yet another example, the method further includes determining that the introducer is advancing at a rate of speed, wherein generating the steering instruction for the introducer is based on the rate of speed.

In another aspect, a video laryngoscope is described. The video laryngoscope includes a handle portion; a display screen coupled to the handle portion; a blade portion, coupled to the handle portion, configured to be inserted into a mouth of a patient; a camera, positioned at a distal end of the blade portion, that acquires a video feed while the video laryngoscope is powered on; a memory storing a trained machine-learning (ML) model; and a processor. The processor operates to receive an indication to automatically steer an introducer. The processor further operates to receive an image of the video feed from the camera in real time, the image including an introducer portion associated with the distal end of the blind introducer. Additionally, the processor operates to classify, by the trained ML model, the image. Based on the classification of the image, the processor operates to generate a steering instruction to steer the distal end of the introducer. The processer also operates to send the steering instruction to a steering system of the introducer to bend the distal end of the blind introducer in the steering direction.

In an example, the image is the only input into the trained ML model. In another example, the manual steering of the introducer at the video laryngoscope is prevented while the automatic steering instructions are sent to the introducer.

In a further aspect, a method for steering a blind introducer via a third-person perspective camera is disclosed. The method includes receiving a video feed from a camera having a third-person view of a blind introducer, the video feed including a distal end of the blind introducer. The method also includes receiving an image from the video feed of the camera. Additionally, the method includes classifying, by a trained machine-learning (ML) model, the image with a classification. Based on the classification, the method includes determining a bending angle for the distal end of the blind introducer. The method further includes instructing a steering system of the blind introducer, in real time, to bend the distal end according to the determined bending angle.

In an example, the image is a first image, the classification is a first classification, and the bending angle is a first bending angle, wherein the method further includes: receiving a second image from the video feed of the camera; and classifying, by the trained ML model, the second image with a second classification, in real time. In another example, the second classification is associated with no action of the distal end of the blind introducer.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

FIGS. 5A-5H are example user interfaces of a video laryngoscope with automatic steering for an introducer.

Figure 1:
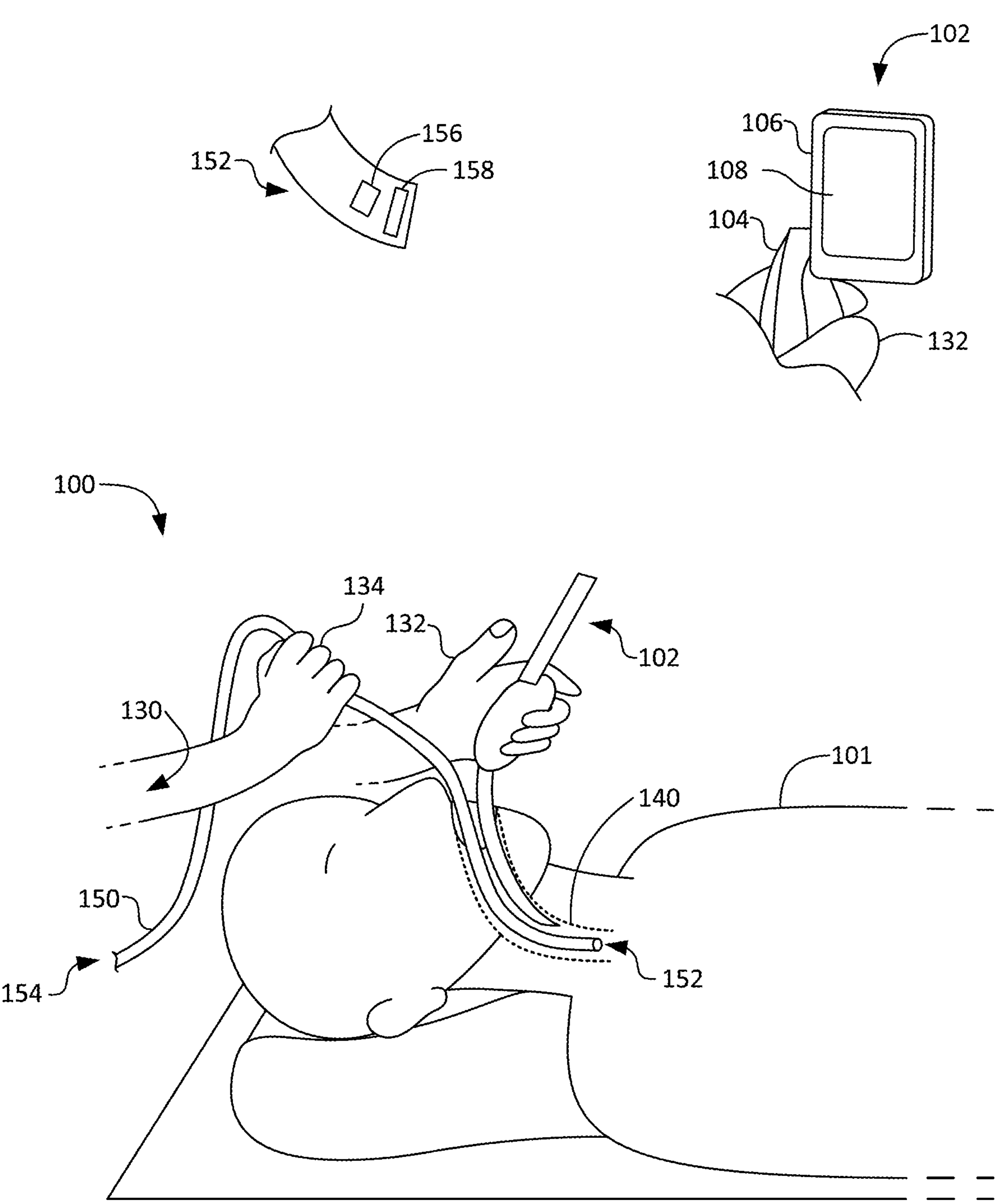
FIG. 1 is a schematic of an example patient environment including a video laryngoscope and an introducer.

While examples of the disclosure are amenable to various modifications and alternative forms, specific aspects have been shown by way of example in the drawings and are described in detail below. The intention is not to limit the scope of the disclosure to the particular aspects described. On the contrary, the disclosure is intended to cover all modifications, equivalents, and alternatives falling within the scope of the disclosure and the appended claims.

DETAILED DESCRIPTION

As discussed briefly above, laryngoscopes are commonly used during intubation of a patient (e.g., an insertion of an endotracheal tube into a trachea of the patient). During intubation, the patient's airway and larynx may be visualized by a medical professional (e.g., a doctor, therapist, nurse, clinician, or other practitioner), such as via video laryngoscopy. In video laryngoscopy, the medical professional may view a real-time video feed of the patient's larynx, other patient anatomy, or other objects or structures in the upper airway of the patient, as captured via a camera of the video laryngoscope and displayed on a display screen of the video laryngoscope. The video feed may assist a medical professional to visualize the patient's airway and facilitate manipulation and insertion of a tracheal tube.

A tracheal tube introducer, otherwise called a bougie, is a long, flexible instrument that may be used to assist in placing a tracheal tube into a patient's trachea during an intubation. Introducers may aid a physician with intubations in difficult airway environments. Some introducers may have a tip, or distal end, which is steerable. For example, the distal end may be actively controllable to bend, turn, rotate, or otherwise move the distal end in a desired direction, such as to navigate through or towards anatomy of the patient. The introducer itself may not have a camera or other visualization component (e.g., the introducer may be blind).

Navigating the introducer into a patient's airway and through a curved path past the vocal cords into the trachea can be challenging. To advance the introducer into a patient cavity, force is often transferred from a proximal portion of the introducer (e.g., from outside of the patient cavity), that results in advancement of the distal end of the introducer within the patient cavity. As used herein, "proximal" refers to the direction out of the patient cavity, back toward a handle end of a device, and "distal" refers to the direction forward into the patient cavity, away from the medical professional, toward the distal end of the introducer. For example, a medical professional holding a proximal portion of the introducer, outside of the patient cavity, pushes downward or forward and the resulting motion is transferred to the distal end of the introducer, causing the distal end to move forward (distally) within the cavity. A pulling force applied by the medical professional at the proximal portion may result in retreat of the distal end or movement in an opposing (e.g., proximal) direction out of the patient cavity. An orientation of the distal end of the introducer may be manually changed by the medical professional by twisting, rotating, or angling, etc. the proximal portion the introducer to cause an associated change in the orientation of the distal end.

The introducer may include steering capabilities via a steerable distal end that is capable of articulating. Articulating or steering the distal end of the introducer then allows for the distal end to guide the introducer through the anatomy of the patient. In an example, steering commands are received at, or by, a controller of the introducer (e.g., a controller of the introducer or a controller communicatively coupled to the introducer, such as a controller of a video laryngoscope, may provide steering commands). Steering commands may be translated into actuation of the distal end of the introducer in an associated, desired direction. Advancement of the distal end of the introducer may be manipulated by a controller (e.g., a forward motor) or may be manipulated manually via force exerted by a medical professional at a proximal portion of the introducer.

During intubation, insertion of a video laryngoscope may result in partial opening or straightening of airway passages due to patient positioning and/or force applied to the laryngoscope to lift the patient's jaw. Coordinating advancement and steering of an introducer using a fixed, third-person perspective view, such as a view from a camera of a video laryngoscope, however, may be challenging. For example, relevant anatomy often referenced to steer the introducer is behind a camera of video laryngoscope properly positioned in a patient's airway. Deflecting the introducer off of anatomy behind the camera (e.g., between the camera and a proximal portion of the introducer, not captured by the video feed), such as to orient and/or advance the distal end of the introducer, may be difficult for a medical professional to achieve due to difficulty in mentally mapping the path of the introducer through the patient's body and when counter-steering the introducer. Additionally, without having a visual reference of other relevant anatomy, an amount of steering may be difficult to approximate due to missing visual information from a third-person perspective camera angle. For instance, from the perspective of a video laryngoscope camera, the tip of the introducer may appear to be deflected at a smaller angle off of the larynx than the actual deflection angle (e.g., may appear 30 degrees off when the distal end of the introducer is actually 90 degrees off). The missing visual information may be compounded with an unseen entrance angle of the introducer, which may cause further difficulties in manually steering the introducer.

Automatic steering of the introducer may assist a medical professional when encountering steering difficulties. Some automatic steering may use image processing to determine a three-dimensional airway environment and/or identify patient anatomy. Identifying anatomical structures and/or medical devices in a video, and resolving the three-dimensional space they represent, however, is computationally expensive and time-consuming. For example, identifying and/or labeling patient anatomy may involve assignment of many pixels and/or a multi-frame analysis and/or annotation of associated image data. Additionally, medical professionals are often familiar with patient airway anatomy and may not benefit from the computationally expensive identification of anatomy in a video feed, despite benefiting from steering assistance.

Provided herein are systems and methods for automatic steering of an introducer, based on a real-time image (e.g., a still-shot) captured from a camera showing a third-person perspective view of the introducer. In examples, automatic steering is determined via artificial intelligence (AI) and/or machine learning (ML) algorithm(s) and/or model(s) applied to a real-time image frame from the camera of a video laryngoscope. The model(s) may be trained based on multiple sets of still-shot training image frames, each set associated with a classification and steering instruction(s) for the introducer. In an example, the real-time image frame input into a trained model is categorized into a class. Based on the class, a steering instruction is determined to steer the introducer. Automatic steering of the introducer may be fully autonomous and/or closed loop, to reduce or prevent interference between automatic and manual steering.

An example patient environment 100 including a video laryngoscope 102 and an introducer 150 is depicted in FIG. 1. The patient environment 100 may be any room where an intubation is being performed, such as a medical suite in a hospital or other care setting, an operating or other procedure room, patient recovery room, an emergency intubation setting, or other environments. As described herein, the video laryngoscope 102 may be used for airway visualization of a patient 101 and/or automatic steering or controlling of a distal end 152 of an introducer 150, based on an image from a camera 116 of the video laryngoscope 102. The video laryngoscope 102 and the introducer 150 may thus both be positionable inside an airway 140 of a patient 101 concurrently, as shown in FIG. 1. Aspects of the video laryngoscope 102 are further shown in FIGS. 2-3 and aspects of the introducer 150 are further shown in FIG. 3.

FIG. 1 shows a medical professional 130 holding a video laryngoscope 102 in a first hand 132 (e.g., a left hand 132 of the medical professional 130) and an introducer 150 in a second hand 134 (e.g., a right hand 134 of the medical professional 130). As further described herein, the video laryngoscope 102 may be positioned in the airway 140 of the patient 101 to manipulate and/or visualize the patient's airway 140, such as with an arm 114 or blade 118. Visualization of the airway 140 of the patient 101 may include viewing patient's anatomy (e.g., larynx, trachea, esophagus, vocal cords, etc.) with a camera 116 of the video laryngoscope 102. The medical professional 130 may move the introducer 150 proximally (e.g., retract the introducer 150) or distally (e.g., advance the introducer 150), while watching the resulting images from the camera 116 of the video laryngoscope 102 on the display 108 of the video laryngoscope 102. The distal end 152 of the introducer 150 may be steered or controlled from the video laryngoscope 102, or based on instructions or classifications provided by the video laryngoscope 102.

The introducer 150 is an elongated, tubular structure through which a tracheal tube may be positioned in the airway 140 of the patient 101. The proximal end 154 of the introducer 150 may communicatively couple with the video laryngoscope 102 such that the introducer 150 may be controlled by, or from, the video laryngoscope 102. The proximal end 154 may be physically coupled to the video laryngoscope 102 such that control systems of the video laryngoscope 102 controls the steering system of the introducer 150. For example, introducer 150 may include a set of pull wires that, when pulled by a steering system, causes the distal end or tip to turn or articulate.

In other examples, the introducer 150 or introducer system may include its own controller or control system that is separate from the video laryngoscope 102. In such examples, coupling between the video laryngoscope 102 and the controller of the introducer may be wired or wireless. If the video laryngoscope 102 and the controller of the introducer 150 are communicating wirelessly, communication may be facilitated by one or more communication devices (e.g., wireless transceivers or hubs, which may be a wireless adapter, dongle, bridge device, etc.) that are configured to establish wireless communication with one another using any suitable protocol.

Steering instructions generated by the video laryngoscope 102 to the introducer 150 may be further based one or more sensor(s) 156 on the introducer 150. For example, the distal end 152 of the introducer 150 may include sensor(s) 156 for determining orientation, inertia, force, etc. of the distal end 152 of the introducer 150. Additionally, the distal end 152 of the introducer 150 may include a light source 158 that may illuminate a path of the introducer 150 and/or reduce shadowing from the introducer 150 associated with a light source of the video laryngoscope 102, which may improve image quality and/or steering accuracy.

Steering or controlling the introducer 150 from the video laryngoscope 102 may be manual, automatic, or assisted. Manual steering or control may be based on input received at the display screen 108 (e.g., touch input) of the video laryngoscope 102 from a medical professional or direct manipulation of the proximal end 154 of the introducer 150. As otherwise described herein, automatic steering or control is determined by a trained model (or models) that process image input from the camera 116 of the video laryngoscope 102. Example automatic steering directions for the distal end 152 of the introducer 150 may include up, down, right, left, right-up, left-up, right-down, left-down, etc. Additionally, steering may include advancing or retracting the introducer 150, such as via a forward-motor control. Assistive or assisted steering or control may be a combination of manual and automatic steering or control of the introducer 150. In assistive steering or control, an amount of steering assistance provided automatically complements any manual steering or control effectuated by a medical professional. In an example, an amount of steering in an assisted control is indirectly proportional to an amount of manual control provided by the medical professional.

Automatic steering of the introducer 150, or any proportional automatic control of the introducer 150 (e.g., assistive steering), may be initiated or triggered. Initiation may be user-specified, such as an input by a medical professional 150 at the video laryngoscope 102 and/or the introducer 150. Additionally or alternatively, automatic steering of the introducer 150 may be triggered when an image acquired by the laryngoscope meets certain criteria. For example, automatic steering may be provided by the video laryngoscope 102 to steer the introducer 150 when certain structures are determined to be visible in the acquired image (e.g., the distal end 152 of the introducer 150, the vocal cords and/or trachea of the patient 101, and/or the esophagus of the patient 101). Determination of object visibility may be based on comparison with training images and may not involve identification or labeling of structures or features in the image itself. In another example, initiation of automatic steering may be conditioned on both a user input (e.g., input at the video laryngoscope 102 and/or the introducer 150) and a later determination that a set of structures are visible in an acquired image of the video laryngoscope 102. Automatic steering may not be provided if the distal end 152 of the introducer 150 is not advancing in the patient (e.g., automatic steering may not be provided if the introducer 150 is stationary or being retracted from the patient 101). Distal or proximal movement of the introducer 150 may be determined based on a comparison of one or more acquired images of the video laryngoscope 102, sensors 122 on the video laryngoscope 102 (e.g., proximity sensor, force sensor, etc.), and/or sensors 156 on the introducer 150 (e.g., inertial measurement unit, orientation sensor, etc.). Images acquired by the video laryngoscope 102 may be stored in a memory 164 of the video laryngoscope 102 for processing to determine classification of an image and/or steering of the introducer 150, as further described herein.

When automatic steering is initiated, and during automatic steering, an indicator may be provided at the video laryngoscope 102 and/or a controller for the introducer 150. For example, a visual indicator may be displayed on a display 108 of the video laryngoscope 102, a light may flash or blink at the video laryngoscope 102 and/or the introducer 150, and/or other visual or haptic feedback may be provided to indicate automatic steering. Additionally or alternatively, a steering direction may be provided on the display 108 of the video laryngoscope 102, such as text (e.g., "right," "up," "left-down," "30 degrees," "45 degrees," "300 degrees," etc.), arrows, angle visual representations, or any other visual indicator associated with a steering direction of the distal end 152 of the introducer 150.

Automatic steering of the distal end 152 of the introducer 150 may be based on a single image captured by the camera 116 of the video laryngoscope 102. The image may be a real-time, still-shot frame from a real-time video feed of a camera, such as a camera 116 of a video laryngoscope 102. The single frame is provided as input to a trained model for analysis to determine a steering classification, steering directions, and/or steering instruction(s) for the distal end 152 of the introducer 150. The single frame may be the only input into the trained model. The trained model may be a neural network, such as a deep-learning neural network or convolutional neural network, among other types of AI or ML models. Other types of models, such as regression models, may also or alternatively be used to classify the images. Training of the model may be based on multiple sets of multiple still-shot images, with each set of still-shot images assigned to a finite quantity of classifications. Training of the AI or ML model is further described with respect to FIG. 6. The trained model may receive and classify the single frame input into one of the finite quantity of classifications, trained based on comparisons or analysis of the sets of still-shot training images. Each classification is associated with a desired steering direction of the distal end 152 of the introducer 150. Because the steering controls of the present technology can be processed by the trained model utilizing a single image for each steering instruction, the trained model and the associated processing can all be performed on the video laryngoscope 102 itself and in real time (e.g., low latency). Other technologies that may require multiple images or continuous processing of the temporal relationships of a video feed require higher processing capabilities and also increase latencies. As such, some of those technologies may not be able to generate a real-time steering instruction locally on the video laryngoscope 102 itself.

An example classification regime for the multiple sets of multiple still-shot images is provided, below, in Table 1.

TABLE 1

| Classification | Steering Direction | Steering Direction Angle |
|---|---|---|
| Class 1 | Up | Bend along 0 degrees |
| Class 2 | Right-Up | Bend along 45 degrees |
| Class 3 | Right | Bend along 90 degrees |
| Class 4 | Right-Down | Bend along 135 degrees |
| Class 5 | Down | Bend along 180 degrees |
| Class 6 | Left-Down | Bend along 225 degrees |
| Class 7 | Left | Bend along 270 degrees |
| Class 8 | Left-Up | Bend along 315 degrees |
| Class 9 | N/A; No Introducer | No Action |
| Class 10 | N/A; No Airway | No Action |

The classification regime shown in Table 1 divides the available 360 degrees of direction angles of the distal end 152 of the introducer 150 within an airway 140 of a patient 101 into eight, mutually exclusive classifications. Although eight steering directions are shown in Table 1, any quantity of steering directions that allows for steering of the introducer 150 in any direction within the airway 140 is appreciated, such as three, four, five, six, seven, or more steering directions. Additionally, although each class with an actionable steering direction in Table 1 is associated with equally distributed steering direction angles (e.g., each steering direction angle is an equal number of degrees away from the next closes steering direction angle, such as 45-degree spacing eight actionable classes), the steering direction angles may not be equally spaced. For example, steering directions in the up, down, right, and left directions may have steering direction angles with smaller distributions (e.g., 20 degrees or less than 45 degrees) and right-up, right-down, left-up, and left-down directions may have steering direction angles with larger distributions (e.g., 70 degrees or more than 45 degrees). A visual representation of the classes shown in Table 1 is provided in FIG. 4B, which is further described, below.

Another example classification regime for the multiple sets of multiple still-shot images is provided, below, in Table 2.

TABLE 2

| Classification | Steering Direction | Steering Magnitude |
|---|---|---|
| Class 1 | Up | Low |
| Class 2 | Up | High |
| Class 3 | Right-Up | Low |
| Class 4 | Right-Up | High |
| Class 5 | Right | Low |
| Class 6 | Right | High |
| Class 7 | Right-Down | Low |
| Class 8 | Down | Low |
| Class 9 | Left-Down | Low |

TABLE 2-continued

| Classification | Steering Direction | Steering Magnitude |
|---|---|---|
| Class 10 | Left | Low |
| Class 11 | Left | High |
| Class 12 | Left-Up | Low |
| Class 13 | Left-Up | High |

Figure 4A:
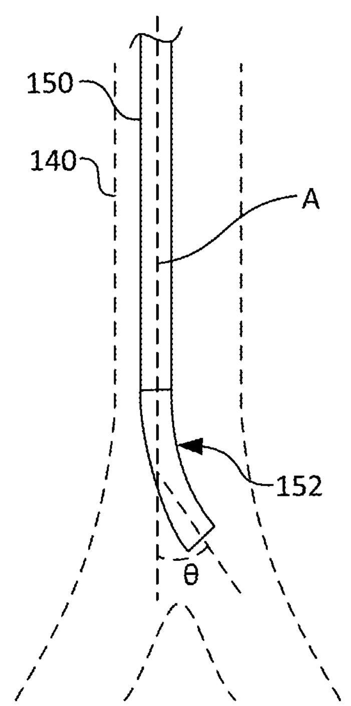
FIGS. 4A-4B show the introducer of FIGS. 1 and 3 in an airway of the patient.

The classification regime shown in Table 2 shows classes that are each associated with a steering direction and a steering magnitude. As described above, a steering direction may be associated with a steering direction angle, from 0 degrees (e.g., gravitationally upward or an "up" steering direction) up to 360 degrees, within the body of the patient 101. A steering magnitude is how much the distal end 152 of the introducer 150 is bent in the steering direction (e.g., a bending angle θ that the distal end 152 of the introducer 150 bends off of a longitudinal axis A of the introducer 150, as shown in FIG. 4A). As shown in Table 2, steering magnitudes may be associated with ranges or steps, such as high, medium, or low. Additionally or alternatively, the steering magnitudes may be associated with a bending angle θ, such as how far the distal end 152 is to be bent (e.g., 20 degrees, 45 degrees, 90 degrees, etc.) As also shown in Table 2, some steering directions may be associated with multiple classifications, each having a different steering magnitude. Although some of the steering directions shown in Table 2 are associated with two steering magnitudes (e.g. classes 1-6 and classes 10-13) and some are associated with one steering magnitude (e.g., classes 7-9), each steering direction may be associated with any number of steering magnitudes (e.g., one, two, three, four, or more magnitudes, such as low, medium, high, any bending angle θ, etc.). Some steering directions may be associated with lower magnitudes to prevent or reduce over-compensation of automatic steering, such as steering directions having a component in a gravitationally downward direction. Although Tables 1 and 2 are provided based on angles (e.g., steering angles and bending angles), any other type of movement vector is appreciated (e.g., cartesian coordinates, coordinate vectors, radians and distance, etc.).

To train a model for the example classification regime shown in Table 1 or Table 2, multiple labeled training images are provided for each class in which a training image is associated with a classification. For instance, training images with a desired steering direction of left are associated with class 7 in Table 1 and either class 10 or class 11 in Table 2 (e.g., with a high or low steering magnitude, depending on how far to the left the distal end 152 is desired to be bent). Additionally, some classifications may be associated with taking no automatic steering action. In the example shown in Table 1, class 9 is associated with no introducer appearing in the training images and class 10 is associated with no airway (e.g., trachea, vocal cords, etc.) appearing in the training images. Other classifications associated with no automatic action are appreciated, such as the introducer being properly positioned for intubation, the introducer being advanced too far into the airway 140, an esophagus not appearing in the images, the camera being too far away from patient anatomy (e.g., trachea, esophagus, vocal cords, etc.), shadows present, unclear image, or other environments where a steering direction of the introducer is unknown or uncertain.

By training the computer vision algorithms (e.g., AI or ML models) on a wide distribution of images for each possible classification, the trained computer vision algorithms can classify a single frame input (e.g., information from an image sensor), in real-time, into one of the possible classifications. To reduce computational energy, the trained model may perform image analysis without identifying, labeling, tracking, or otherwise detecting anatomy or structures within the input image. The classification may be performed by a processor 162 of the video laryngoscope 102 and/or a processor 176 of the controller for the introducer 150 (e.g., the trained model may be deployed on the video laryngoscope 102 and/or the introducer 150). The single frame input image and the training images may be stored in memory 164 of the video laryngoscope 102 and/or memory 178 of the controller of the introducer 150. In some examples, the trained model may be updated in non-run time. For example, after classification of any single-frame input image, that input image may be added to the set of training images for its determined classification. The updated set of training images may then be used to later train or update the model.

After an input image is categorized into a class, a steering instruction or movement vector is determined for the distal end 152 of the introducer 150. The steering instruction/movement vector is associated with the determined class for the input image. In the example shown in Table 1, above, class 1 is associated with a steering instruction/movement vector of bending the introducer upwards, class 2 associated with a leftward-upward bend, class 3 associated with a leftward bend, etc. In the example shown in Table 2, above, class 1 is associated with a steering instruction/movement vector of bending the introducer upwards at a small bending angle θ, class 2 associated with an upward bend at a large bending angle θ, class 3 associated with a rightward-upward bend at a small bending angle θ, etc. In some examples, the steering control may be the direct classification output of the ML model. For instance, the classification of an image may be "steer left." When determining the steering instructions, a visual indicator of steering direction may be displayed at a display 108 of the video laryngoscope 102 (e.g., as shown in FIGS. 5A-5F).

The steering magnitude may be constant or specified as part of a classification (e.g., as shown in Table 2). Alternatively, the steering magnitude may be based on, or proportional to, actions by the medical professional 130 (e.g., assistive steering). For example, the introducer 150 may be steered more strongly (e.g., at a greater magnitude) if less manual steering input is concurrently provided by a medical professional (e.g., slow rate of speed of advancement of the introducer 150, minor manual movement or bending of the introducer 150, minor or slow steering input at the video laryngoscope 102, etc.). In an alternative example, the introducer 150 may be steered less strongly (e.g., a smaller magnitude) if more manual steering input is concurrently provided by a medical professional (e.g., rapid rate of speed of advancement of the introducer 150, frequent or major manual movement or bending of the introducer 150, frequent or rapid steering input at the video laryngoscope 102, etc., so as to not result in conflicting or undesirable movement of the introducer 150). In some instances, manual steering of the introducer 150 from the video laryngoscope 102 (e.g., user input as a user interface of the video laryngoscope 102) is prevented or dampened while the automatic steering instructions being used to steer the introducer 150.

The steering instruction/movement vector, associated with the determined class of the input image, may be determined by a processor 162 of the video laryngoscope 102 or a processor 176 of the controller of the introducer 150. In an example where the class is determined by the processor 176 of the controller of the introducer 150, the processor 176 of the introducer 150 may determine the steering instruction/movement vector. As discussed herein, the controller of the introducer 150 in some cases is included in or coupled to the video laryngoscope 102. If the class is determined by a processor 162 of the video laryngoscope 102 and the introducer 150 has a separate controller, the processor 162 of the video laryngoscope 102 may determine the steering instruction/movement vector and send the steering instruction/movement vector to the controller of the introducer 150 for actuation of steering the distal end. Alternatively, a class determined by a processor 162 of the video laryngoscope 102 may be sent to the controller of the introducer 150 for determining the steering instruction/movement vector at the processor 176 of the introducer 150. The steering instruction/movement vector may be modified or generated based on measurements from sensor(s) 156 of the introducer 150 (e.g., inertial movement unit, gyroscope, orientation sensors, etc.). For example, sensor measurements from the introducer 150 may be used to align the steering instruction/movement vector with the orientation of the introducer 150 to correlate implemented movement of the introducer 150 with the intended or desired direction of the steering instruction/movement vector.

Automatic steering of the introducer 150 may persist in a continuous loop. In a continuous loop analysis, contemporaneous image frames may be analyzed by the trained model(s) in real time. For example, each image frame of a video feed (e.g., frames acquired at 30 frame per second) may be analyzed. In another example, a subset of the total image frames of a video feed may be analyzed. For instance, every second, third, fourth, etc. frame may be analyzed. Alternatively, image frames may be analyzed in preset intervals (e.g., every 0.1 seconds, every 0.2 seconds, etc.) as may be tracked by a timer 172 of the video laryngoscope 102. As another alternative, the frequency of image frame analysis may be based on rate of advancement speed of introducer 150 (e.g., image frames analyzed at a greater frequency with faster distal or proximal movement of the introducer 150, image frames analyzed at a lesser frequency with slower distal or proximal movement of the introducer 150, little to no frame analysis when the introducer 150 is not moving, etc.).

Figure 2:
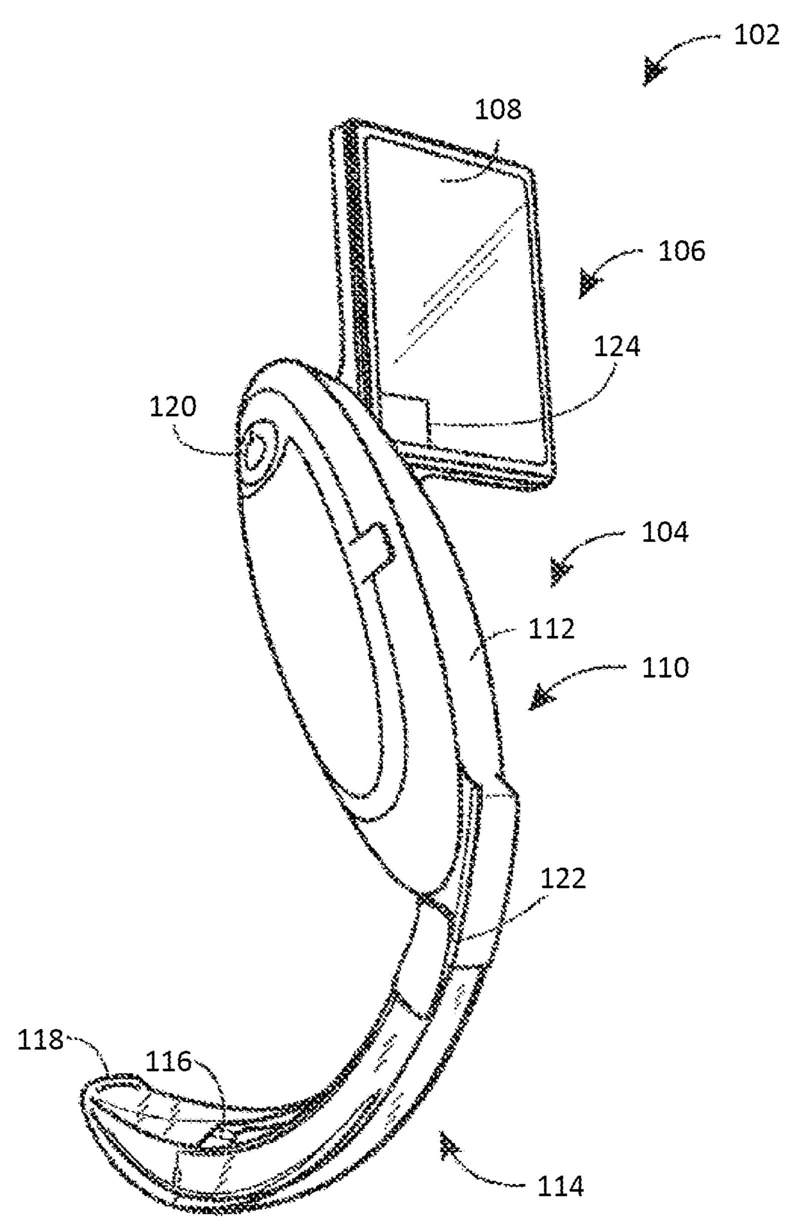
FIG. 2 is a schematic of the video laryngoscope of FIG. 1.

FIG. 2 shows a perspective view of a video laryngoscope 102. As shown, the video laryngoscope 102 has a body 104 (e.g., reusable body). The body 104 includes a display portion 106 having a display screen 108 that is configured to display images and/or other data, a handle portion 110 having a handle 112 that is configured to be gripped by the medical professional during the laryngoscopy procedure, and an elongate portion or arm 114 that supports a camera 116 and light source (e.g., light-emitting diodes (LEDs)) that is configured to obtain images, which may be still-shot images and/or moving images (e.g., a video feed). The camera 116 and light source may be incorporated on the distal end of the arm 114. The light source may be provided as part of the camera 116 or separate from the camera 116 on the blade 118 or arm 114.

In examples, the display portion 106 and the handle portion 110 may not be distinct portions, such that the display screen 108 is integrated into the handle portion 110. In the illustrated embodiment, an activating cover, such as a removable laryngoscope blade 118 (e.g., activating blade, disposable cover, sleeve, or blade), is positioned about the arm 114 of the body 104 of the laryngoscope 102. Together, the arm 114 of the body 104 and the blade 118 form an insertable assembly that is configured to be inserted into the patient's oral cavity. It should be appreciated that the display portion 106, the handle portion 110, and/or the arm 114 that form the body 104 of the laryngoscope 102 may be fixed to one another or integrally formed with one another (e.g., not intended to be separated by the medical professional during routine use) or may be removably coupled to one another (e.g., intended to be separated by the medical professional during routine use) to facilitate storage, use, inspection, maintenance, repair, cleaning, replacement, or interchangeable parts (e.g., use of different arms or extensions with one handle portion 110), for example.

The handle 112 and/or arm 114 may include one or more sensors 122 capable of monitoring functions (e.g., different, additional, and/or advanced monitoring functions). The sensors 122 may include a torque sensor, force sensor, strain gauge, accelerometer, gyroscope, magnet, magnetometer, proximity sensor, reed switch, Hall effect sensor, etc. disposed within or coupled to any suitable location of the body 104. The sensors 122 may detect interaction of the video laryngoscope 102 with other objects, such as a blade 118, physiological structures of the patient (e.g., teeth, tissue, muscle, etc.), or proximity of an introducer (e.g., introducer 150).

The laryngoscope 102 may also include a power button 120 that enables a medical professional to power the laryngoscope 102 off and on. The power button 120 may also be used as an input device to access settings of the video laryngoscope 102, including a mode of operation (e.g., manual, automatic, or assistive steering of an introducer 150). Additionally, the video laryngoscope 102 may include an input button, such as a touch or proximity sensor 124 (e.g., capacitive sensor, proximity sensor, or the like) that is configured to detect a touch or object (e.g., a finger or stylus). The touch sensor 124 may enable the medical professional operating the video laryngoscope 102 to efficiently provide inputs or commands, such as inputs to select a mode of steering for an introducer 150 (e.g., manual, automatic, or assistive), inputs that cause the camera 116 to obtain or store an image on a memory of the laryngoscope, and/or any other inputs relating to function of the video laryngoscope 102.

Figure 3:
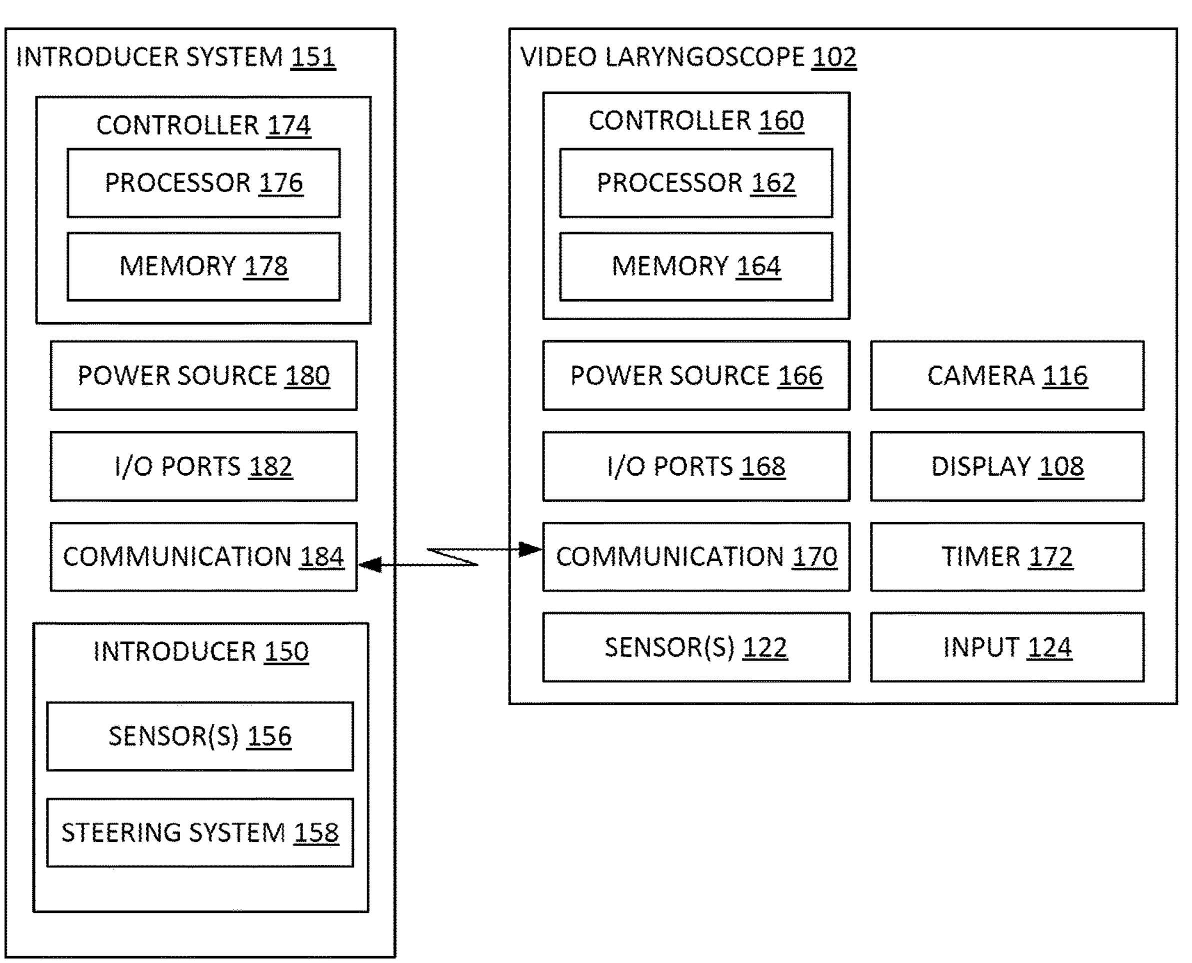
FIG. 3 is a block diagram of components of the video laryngoscope and the introducer of FIG. 1.

FIG. 3 is a block diagram of components of the video laryngoscope 102 and the introducer system 151. As shown, the video laryngoscope 102 and/or the introducer system 151 may include various components that enable the video laryngoscope 102 to carry out the techniques disclosed herein. For example, the video laryngoscope 102 may include the display screen 108, the camera 116, a light source (e.g., which may integrated into the camera or separate from the camera), sensor(s) 122, and input (e.g., touch sensor) 124, as well as a controller 160 (e.g., electronic controller), one or more processors 162, a hardware memory 164, a power source (e.g., battery) 160, input/output (I/O) ports 168, a communication device 170, and a timer 172. In some embodiments, the timer 172 may track relative time (e.g., a start time, an end time, a frequency of image frame sampling), which may be referenced to acquire still-shot input images for analysis.

The introducer system 151 may include a controller 174 (e.g., electronic controller), one or more processors 176, a hardware memory 178, a power source (e.g., battery or input from external power source) 180, I/O ports 182, and a communication device 184. The power source 180 may be rechargeable batteries, replaceable batteries, and/or pull power from a power source 166 of the video laryngoscope 102. While the controller 174, power source 180, I/O ports 182, and communication devices 184 are depicted as being separate from the video laryngoscope 102, one or more of those components may be provided within the video laryngoscope 102 and/or may be omitted where the video laryngoscope 102 controls or steers the introducer 150.

The introducer system 151 also includes the introducer 150, which includes one or more sensors 156 (e.g., orientation sensors, inertial measurement units, gyroscopes, proximity sensors, force sensors, etc.) and a steering system 158. The steering system 158 may include pull wires connected to the distal end of the introducer 150. When tension of a particular pull wire is increased, the distal end is caused to bend towards that pull wire. Accordingly, the steering system 158 may also include tension-generating components, such as motors. Other types of steering systems 158 are also possible that are capable of causing the physical steering or bending of the distal end of the introducer 150.

In examples where the controller 174 for the introducer 105 is separate from the video laryngoscope 102, the communication devices 170, 184 may enable wired or wireless communication. The communication devices 170 of the video laryngoscope 102 may communicatively couple with the communication devices 184 of the introducer system 151 to allow communication between the video laryngoscope 102 and the introducer system 151 (e.g., sending or receiving signal between the devices). For example, the video laryngoscope 102 and/or the introducer system 151 may relay acquired input images, image classification, and/or steering instructions/movement vectors for analysis, control, storage, and/or other interaction. Wireless communication may include transceivers, adaptors, and/or wireless hubs that are configured to establish and/or facilitate wireless communication with one another. By way of example, the communication devices 170, 184 may be configured to communicate using the IEEE 802.15.4 standard, and may communicate, for example, using ZigBee, WirelessHART, or MiWi protocols. Additionally or alternatively, the communication devices 170, 184 may be configured to communicate using the Bluetooth standard or one or more of the IEEE 802.11 standards.

In some examples, the video laryngoscope 102 and/or the introducer system 151 include electrical circuitry configured to process signals, such as signals generated by the camera 116 or light source, signals generated by the sensor(s) 122, 156, and/or control signals provided via inputs 124 or automatically. The processors 162, 176 may be used to execute software. For example, the processor 162 of the video laryngoscope 102 may be configured to receive signals from the camera 116 and light source and execute software to acquire an image, analyze an image, classify an image, generate steering instructions, etc.

The processors 162, 176 may include multiple microprocessors, one or more "general-purpose" microprocessors, one or more special-purpose microprocessors, and/or one or more application specific integrated circuits (ASICS), or some combination thereof. For example, the processors 162, 176 may include one or more reduced instruction set (RISC) processors. It should be appreciated that the various processing steps may be carried out by either processor 162, 176 or may be distributed between the processors 162, 176 in any suitable manner.

The hardware memory 164, 178 may include a volatile memory, such as random access memory (RAM), and/or a nonvolatile memory, such as read-only memory (ROM). It should be appreciated that the hardware memory 164, 178 may include flash memory, a hard drive, or any other suitable optical, magnetic, or solid-state storage medium, other hardware memory, or a combination thereof. The memory 164, 178 may store a variety of information and may be used for various purposes. For example, the memory 164, 178 may store processor-executable instructions (e.g., firmware or software) for the processors 162, 176 to execute, such as instructions for processing signals generated by the camera 116 to generate the image, provide the image on the display screen 108, analyze an image via a trained model, determine a classification for an image, determine steering instructions/movement vectors associated with an image, etc. The hardware memory 164, 178 may store data (e.g., acquired images, training images, classification information, steering instructions/movement vectors, AI or ML algorithms, trained models, tags or labels, mode data, etc.), instructions (e.g., software or firmware for generating images, storing the images, analyzing the images, classifying the images, determining steering instructions, etc.), and any other suitable data.

Figure 4B:
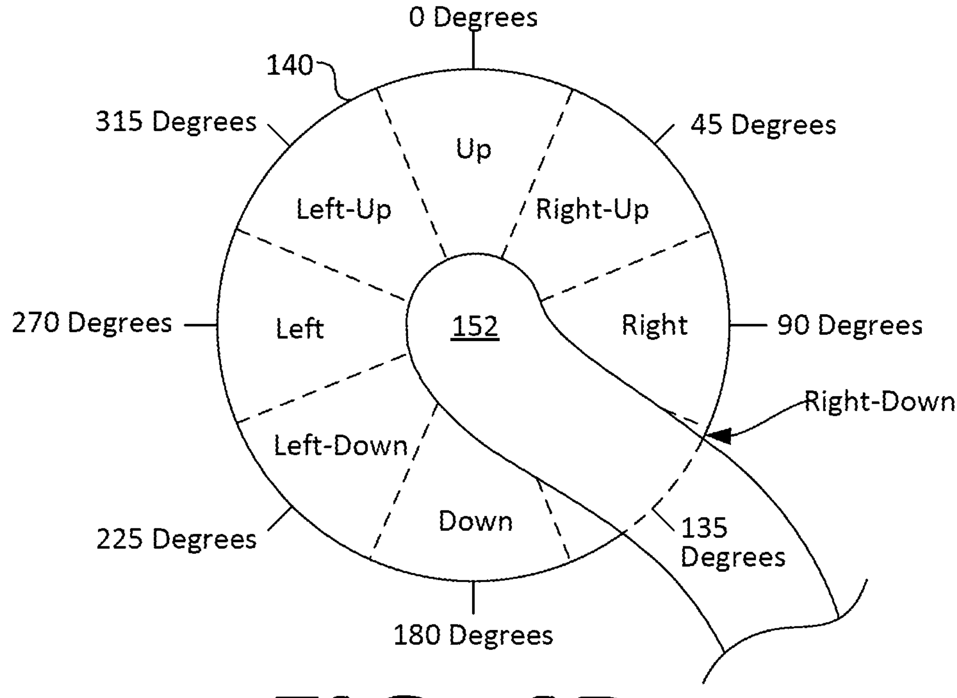

FIGS. 4A and 4B show the introducer 150 of FIGS. 1 and 3 in an airway 140 of the patient 101. Referencing FIG. 4A, a cross-sectional view of the patient's airway 140 cut along a length of the airway 140 is shown. As described herein, the distal end 152 of the introducer 150 may be steered or controlled. The distal end 152 of the introducer 150 may steer by bending, turning, rotating, curving, or other movement. For example, the distal end 152 of the introducer 150 may bend up to 90 degrees in any direction or dimension (not just in a single plane, such as up/down or right/left), enabling steering of the distal end 152 of the introducer 150 within a hemisphere. As otherwise described herein, a bending angle θ, off of which the distal end 152 of the introducer 150 is bent from a longitudinal axis A, is a steering magnitude. Alternatively, steering direction angles, associated with the steering direction, are further described in FIG. 4B. Steering may be implemented via an actuation system, including one or more actuators (e.g., sleeved pull-wires or other actuators), which move to bend or un-bend the distal end 152 of the introducer 150 into or out of a curved or bent shape. Some examples of a steerable endoscope, for which some steering aspects may be similar to a steerable introducer, are described in U.S. patent application Ser. No. 16/995,181, filed Aug. 17, 2020, the entirety of which is hereby incorporated by reference.

FIG. 4B shows a cross-sectional view of the patient's airway 140 cut across the length of the airway 140. The example shown in FIG. 4B divides the airway 140 of the patient 101 into eight steering directions (e.g., the distribution of steering directions provided as an example in Table 1, above), each associated with a steering angle (e.g., 0, 45, 90, 135, 180, 225, 270, and 315-degree steering angles). In FIG. 4B, the distal end 152 of the introducer 150 is steering into the page in a left-up direction (e.g., the distal end 152 is bent toward a steering angle of 315 degrees off of "up," in a left-up direction, such as provided in class 8 of Table 1). A bend in an upward direction may be a bend in an anterior direction, towards the patient's chest and opposite gravity, and a bend in a downward direction may be a bend in a posterior direction, towards the patient's back and with gravity. Likewise, a bend in a right direction may be a bend towards a right-hand side of the patient 101 and a bend in a left direction may be a bend towards a left-hand side of the patient 101. Steering directions are associated with steering instructions/movement vectors. As further described above, magnitude of bend of the distal end 152 of the introducer 150 may be class-assigned, constant, or assistive, based on an amount of control perceived to be exerted by the medical professional 130.

FIGS. 5A-5H are example user interfaces of a video laryngoscope 102 with automatic steering for an introducer (e.g., introducer 150). As described herein, a camera 116 of the video laryngoscope 102 may capture a view of the distal end of the introducer in relation to patient upper airway anatomy. The images from the captured view are displayed on a display 108 of the video laryngoscope 102. Some or all of the image frames may be analyzed using the AI or ML models described herein.

Figures 5A, 5B:
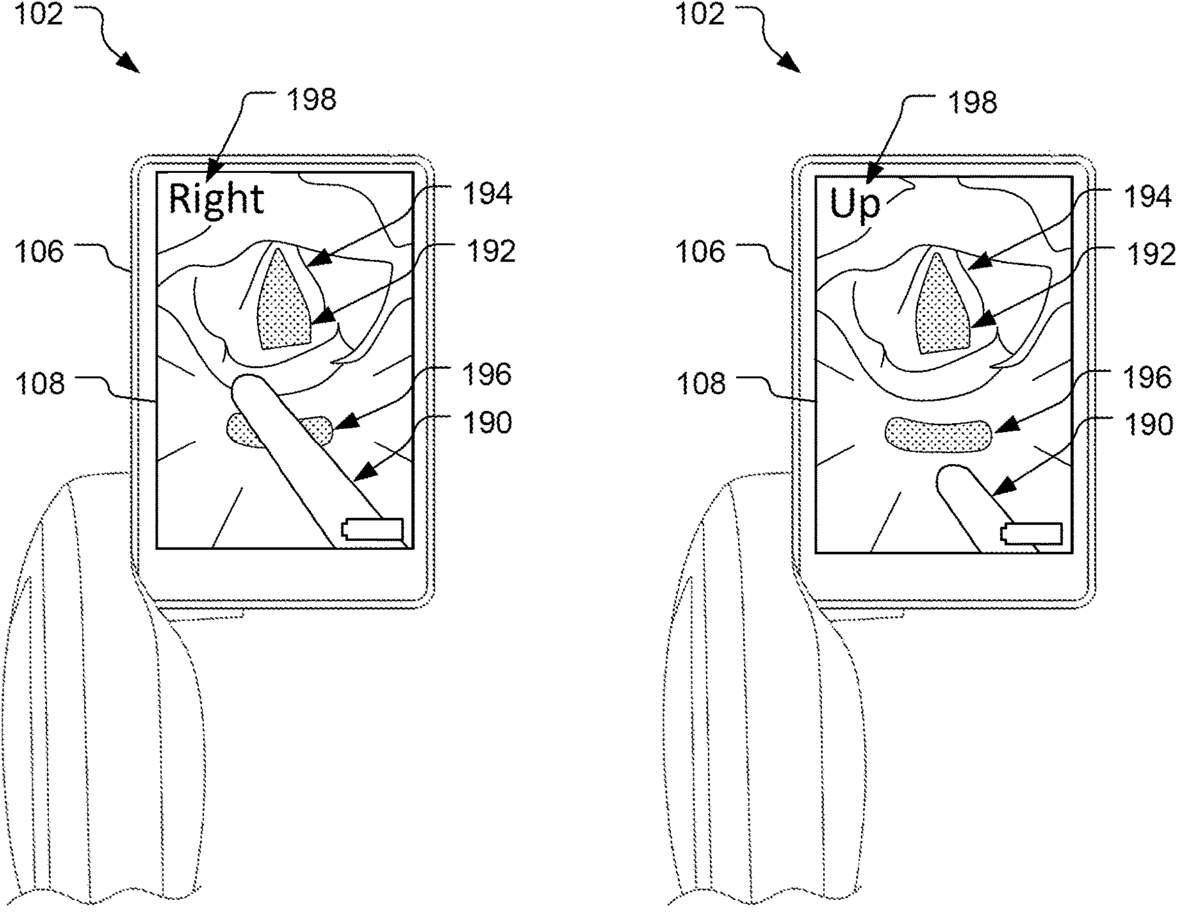
Figures 5C, 5D:
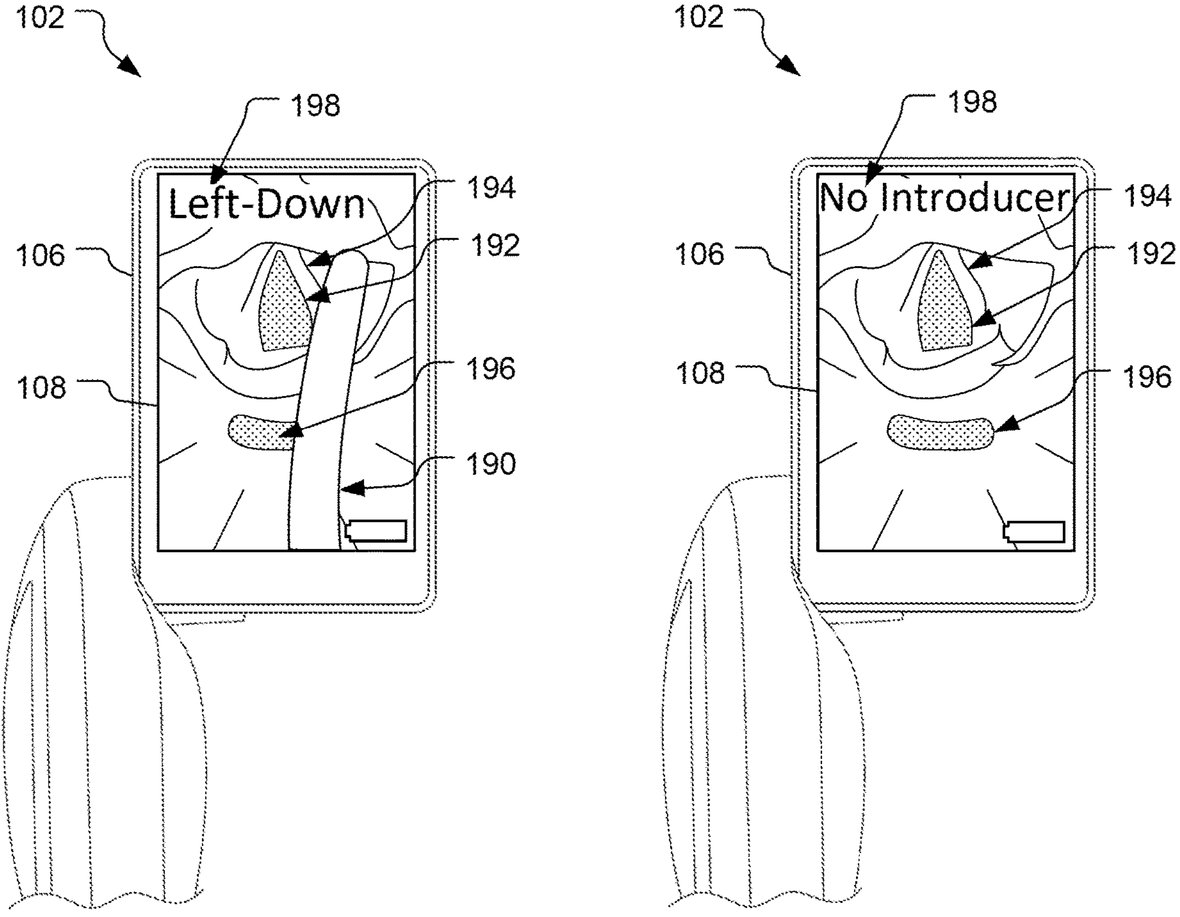

FIGS. 5A-5C show example still-shot images that have been analyzed by AI or ML models and classified within a class and associated with steering instructions/moving vectors. The still-shot images shown in FIGS. 5A-5C include an introducer portion 190, a trachea portion 192, a vocal cord portion 194, an esophagus portion 196, and a steering indicator 198. The portions of the images associated with the introducer (e.g., introducer 150) or with patient anatomy may be determined based on visual analysis by the trained model. The portions of the images may not be otherwise assigned, labeled, tagged, or otherwise specifically identified (e.g., the anatomical structures and/or introducer may not be specifically identified or labeled). In FIG. 5A, the image shown on the display 108 is classified based on visual similarities to training images grouped in a class associated with steering right (e.g., as indicated with steering indicator 198). The image shown on the display 108 of FIG. 5B is classified based on visual similarities to training images grouped in a class associated with steering up (e.g., as indicated with steering indicator 198). In FIG. 5C, the image shown on the display 108 is classified based on visual similarities to training images grouped in a class associated with steering left-down (e.g., as indicated with steering indicator 198).

FIGS. 5D-5F show example still-shot images that have been analyzed by a trained model and classified within a class that is associated with no steering action. No steering action may result when at least one element or portion in the still-shot image is missing, such as portion of the image associated with the introducer (e.g., introducer portion 190) or associated with patient anatomy (e.g., a trachea portion 192, a vocal cord portion 194, an esophagus portion 196). In such a situation, there may not be enough visual reference information to determine an appropriate steering direction. Alternatively, no steering action may result when the introducer portion 190 is determined to be properly positioned for intubation, such as the image displayed in FIG. 5F. The steering indicator 198 may visually indicate that no steering action is determined (e.g., text reading "no action" or other text or visual indicator or symbol may appear on the display 108). Additionally or alternatively, the steering indicator 198 may provide information about why no action is determined, such as no introducer (e.g., as shown in FIG. 5D), no airway, proper positioning, introducer advanced too far, laryngoscope camera not properly positioned, image obscured or unclear, etc.

Figures 5G, 5H:
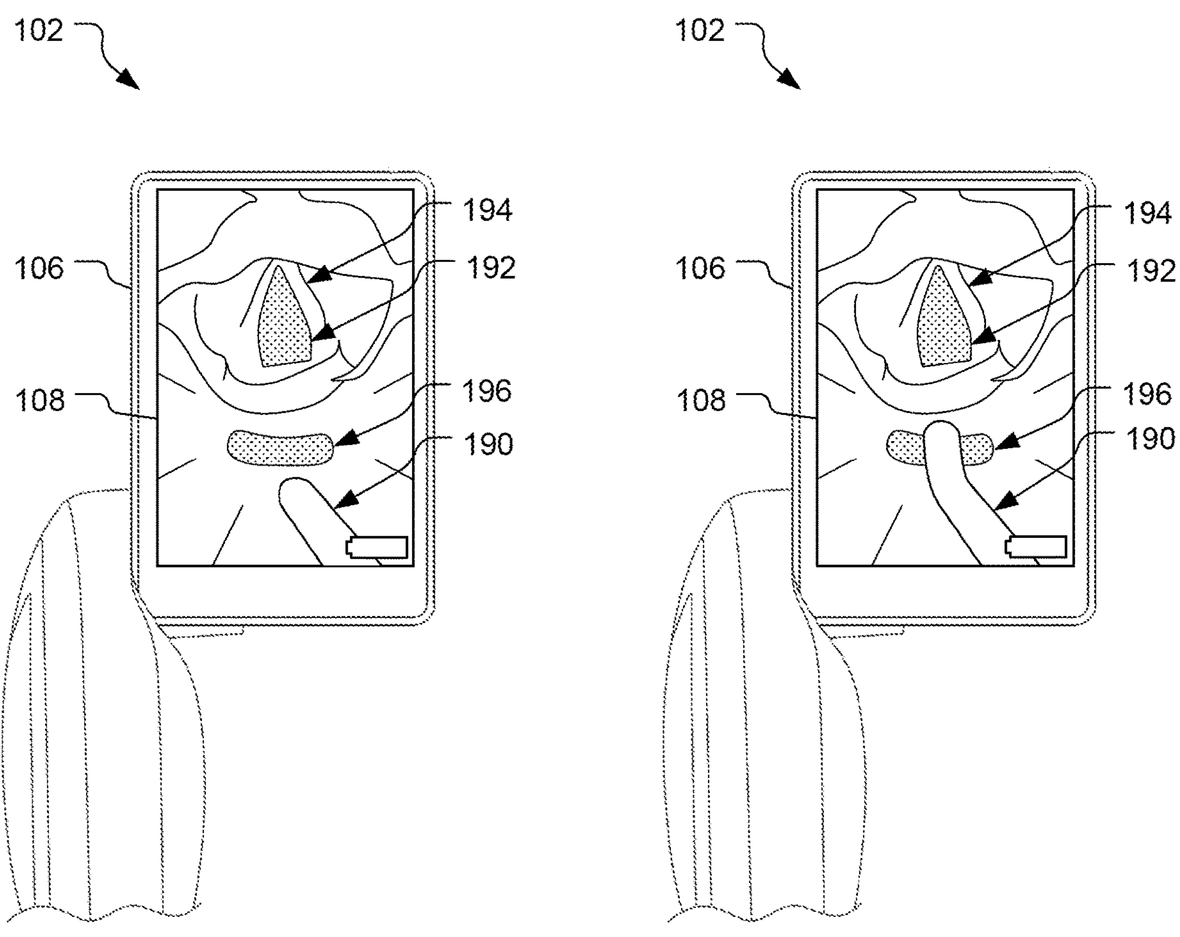

FIGS. 5G-5H show example still-shot images that have been analyzed by a trained model, classified, and associated with steering instructions/moving vectors to automatically steer an introducer without a steering indicator (e.g., without steering indicator 198). For example, the still-shot image of FIG. 5G may be analyzed by a trained model to determine a steering direction of "up." As a user advances the introducer 150, without manually steering the introducer 150, the distal end 152 of the introducer 150 may be automatically bent upwards, which may result in the positioning shown in FIG. 5H.

Figure 6:
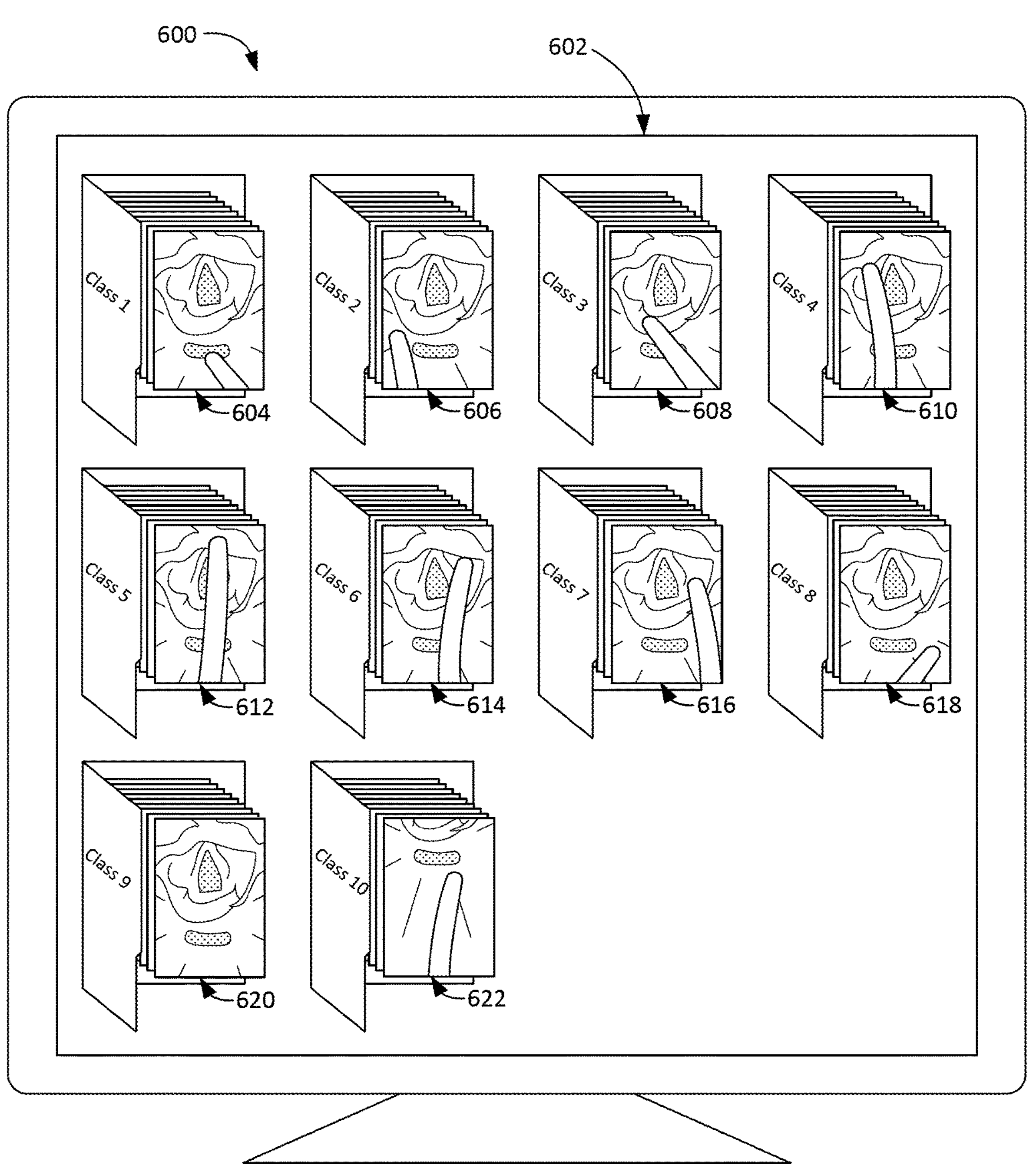
FIG. 6 shows example training images grouped by classification on a display.

FIG. 6 shows example training images 604-622 grouped by classification on a display 602 of a computing system 600. The classification groupings shown for the training images in FIG. 6 may be similar to the classifications described in Table 1, above. Training of the AI or ML model may be based on multiple sets of multiple still-shot training images 604-622, with each set of still-shot images assigned to a finite quantity of classifications (e.g., in the example shown in FIG. 6, ten classes). The sets of training images 604-622 for each classification may be stored in a different folder for each classification. A trained model may be based on the training images 604-622 to generalize or classify an input image into one of the finite quantity of classifications (e.g., classes 1-10 shown in FIG. 6). Each classification is associated with a desired steering direction of the distal end 152 of the introducer 150.

Figure 7:
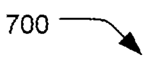
FIG. 7 is a flow diagram of an example method of steering an introducer with a camera of a video laryngoscope.
Figure 7:
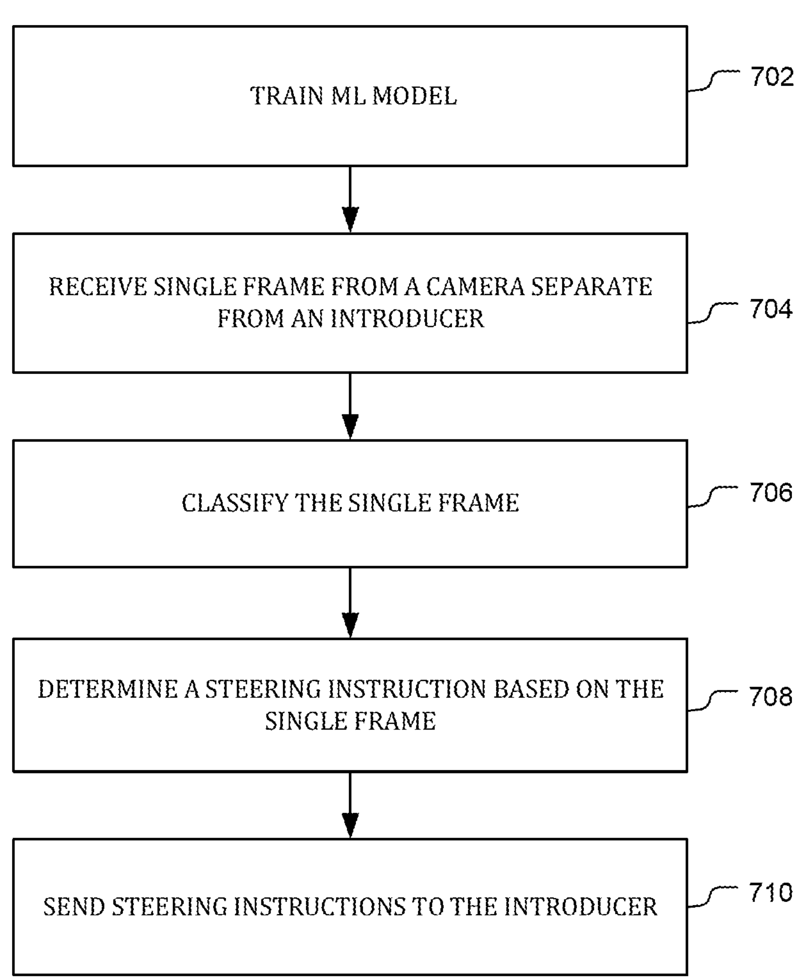

FIG. 7 shows an example method 700 according to the disclosed technology. The example method includes operations that may be implemented or performed by the systems and devices disclosed herein. For example, the video laryngoscope 102 and/or introducer 150 depicted in at least FIGS. 1-3 may perform the operations described in the methods. In addition, instructions for performing the operations of the methods disclosed herein may be stored in a memory of the video laryngoscope and/or remote device (e.g., system memories 164, 178 shown in FIG. 3).

More specifically, method 700 is an example method of steering an introducer with a camera of a video laryngoscope. At operation 702, model(s) are trained with a set of training images that have been pre-classified either through manual or other classification techniques. The model is trained to output a steering classification, steering directions, and/or steering instructions for a distal end of an introducer, based on a single image frame input. Training of the AI or ML models may be based on multiple sets of multiple still-shot images, with each set of still-shot images assigned to a classification that is associated with a desired steering direction of the distal end of the introducer. For example, a first set of training images is associated with a first class and a first steering direction, and a second set of training images associated with a second class and a second steering direction.

At operation 704, a single image frame is received from a camera. The camera may be separate or independent from the introducer, such that the single frame shows a third-person perspective view of the introducer. In an example, the camera may be a camera of a video laryngoscope. The single frame may be extracted or received as part of a real time video feed. For example, when a video laryngoscope is powered on, images from a camera of the video laryngoscope may automatically be captured. Acquired images may be recorded, stored, analyzed, etc. The single frame image (e.g., to an input into the trained model described at operation 702) may be received in response to an indication to automatically steering an introducer (e.g., a steering mode initiated via user input).

Initiation of automatic steering (e.g., which may be a mode of operation of the introducer, a video laryngoscope, or other device hosting a camera with a third-person perspective view of the introducer) may be based on image analysis and/or user input. For example, initiation of the automatic steering (e.g., receiving a single frame or determining a classification for the single frame, as further discussed at operation 706) may be based on a portion of the image being associated with an introducer and/or based on a portion of the image being associated with patient anatomy (e.g., trachea, vocal cords, esophagus, etc.). Alternatively, automatic steering may be on or available whenever image frames are being acquired by a third-person perspective view camera (e.g., when a video laryngoscope is powered on).

At operation 706, the single frame is classified. Classification outputs for the trained model may be of a finite quantity. For example, there may be between 2-360 output classifications. The output classifications may be associated with a steering direction in which steering the distal end of the introducer would be desirable (e.g., steering angles between 0-360 degrees within a body of the patient, towards which the distal end of the introducer is desired to be steered) or any other movement vector. Additionally, output classifications may also be associated with a steering magnitude (e.g., how strongly to bend the distal end of the introducer). Some classifications may be associated with no action or movement of the introducer, such as no introducer portion determined (e.g., as shown in FIG. 5D), no patient anatomy portion determined, proper positioning of the introducer, introducer advanced too far, laryngoscope camera not properly positioned, image obscured or unclear, introducer not advancing, etc.

At operation 708, a steering instruction is determined, based on the single frame. As further described herein, each classification is associated with either an action or no action for the introducer. Action-associated classifications may have a steering instruction that is a steering angle and/or a steering magnitude (e.g., a bending angle), cartesian or three-dimensional coordinate positioning, or any other movement vector. Classifications associated with no action may deliver a steering instruction without a movement vector (e.g., do not steer or do not change the prior or current steering instruction). In an example with two output classifications, a first classification may be associated with an image of the introducer positioned through the vocal cords (e.g., proper placement) and steering instruction to straighten the introducer, and a second classification may be no action. In an example with several output classifications, multiple classifications may be associated with an action and multiple classifications may be associated with no action (e.g., see Table 1).

At operation 710, the steering instruction is sent. If a processor associated with the third-person view camera (e.g., a processor of a video laryngoscope) determines the steering instruction, the steering instructions are sent from the processor to the steering system for the introducer. When the steering system receives the steering instructions, implementing of the instructions is provided in real time such that the introducer steers the distal end in real time (e.g., low latency, such as less than 100 milliseconds, etc.). When a steering instruction is sent, a visual indicator may be provided at a user interface associated with the camera (e.g., at a display of a video laryngoscope) and/or a user interface of the introducer. Additional data, information, and/or indicators may also be displayed on the video laryngoscope. For instance, sensor information from sensors of the video laryngoscope or the introducer, steering direction or instruction, etc. The introducer may prevent manual user input from being received while receiving a steering instruction.

Operations 704-710 may repeat as required or desired. For example, image frames may be input and analyzed in real time (e.g., at 50 frames per second or a lesser sampling frequency). For example, a first frame may be analyzed and associated with a first classification or first steering instruction contemporaneously before a second frame is analyzed and associated with a second classification or second steering instruction. This may persist in a continuous loop until automatic steering is terminated (e.g., user input is received to end automatic steering, the introducer is removed from the patient and/or no longer communicatively coupled with the third-person camera source or video laryngoscope, the patient is intubated, a portion of the frame is not associated with an introducer for a threshold period of time, etc.).

Figure 8:
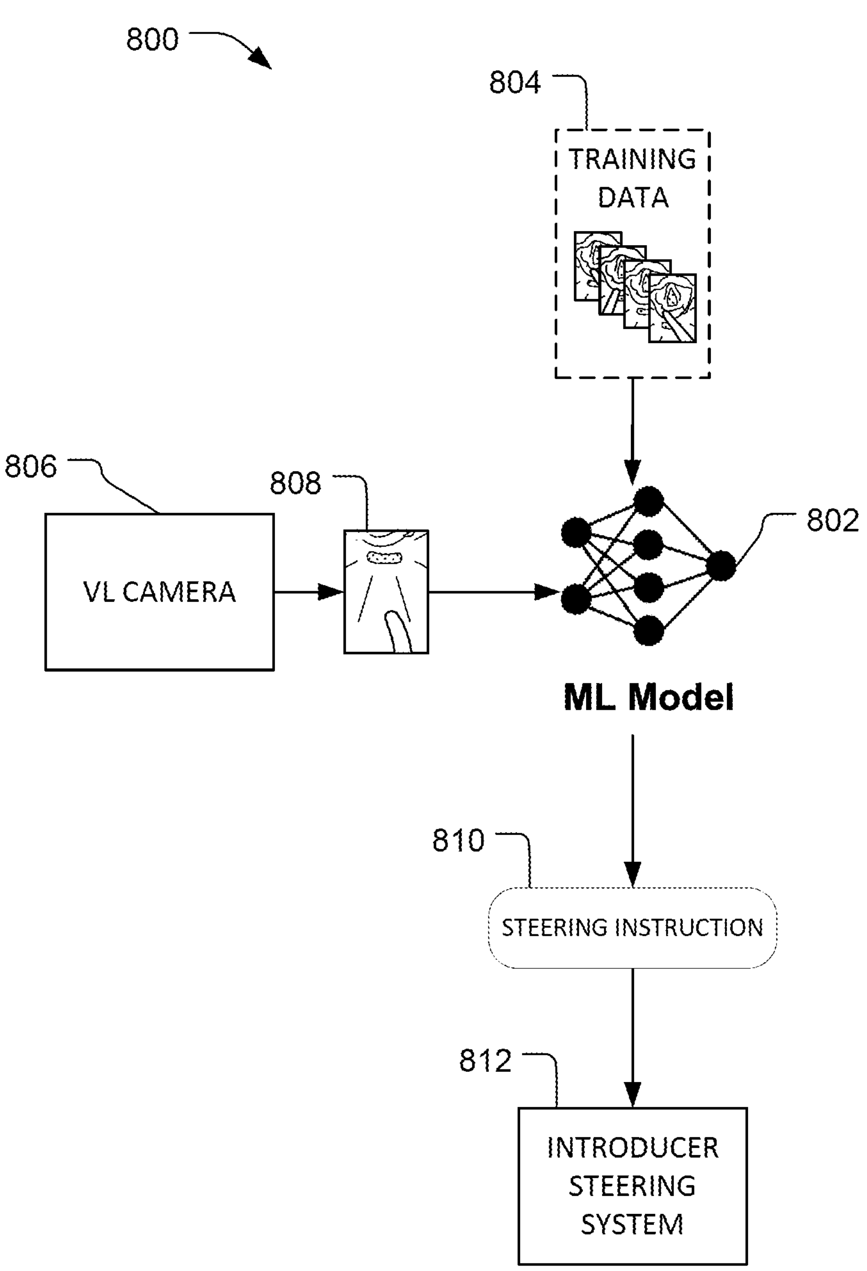
FIG. 8 depicts an example data flow for automatically steering a distal end of an introducer.

FIG. 8 depicts an example data flow 800 for automatically steering a distal end of an introducer (e.g., distal end 152 of introducer 150). As discussed above, a trained model 802 is utilized to classify real-time images 808 from a video laryngoscope camera 806. The trained model 802 has been trained based on a set of training data 804. The trained model 802 may be trained prior to its deployment/installation on the video laryngoscope or respective controller. The training data 804 includes a large set of images that are labeled with respective corresponding classifications, which may include a steering direction and, in some cases, a steering magnitude for the steering direction. In an example, magnitudes may have various ranges or steps, such as high, medium, or low. In other examples, the magnitudes may be associated with a bending angle, such as how far the distal end is to be bent (e.g., 20 degrees, 45 degrees, 90 degrees, etc.). Each pairing of a direction and magnitude may be considered a separate class. As an example, a steering instruction of "Direction: Left; Magnitude: High" may be considered one class, and a steering instruction of "Direction: Left; Magnitude: Low" may be considered another class. In other examples, magnitude values may be omitted from the classifications and steering instructions and/or may be predetermined, preset, or constant.

The training data 804 may be labeled with the corresponding classes via manual classifications or through other methods of labeling images. The trained model 804 may then be trained with the training data set using a supervised or semi-supervised training method or algorithm that utilizes the classified images in the training data 804. Once the trained model 804 is generated, the trained model 804 may be used to generate steering instructions in real time.

For example, the video laryngoscope camera 806 generates live or real-time images 808. The real-time image is provided as input to the trained model 802. The trained model 802 processes the received input image 808 and classifies the image 808. The classification of the image 808 corresponds to a steering instruction 810. The steering instruction 810 may be the direct output of the trained model in some examples. In other examples, the classification (e.g., output from the trained model 802) is further processed to generate the steering instruction 810. In either example, the steering instruction is based on the classification of the real-time image 808 from the trained model 802.

The steering instruction 810 is provided to the introducer steering system 812, which, as discussed above, may include one or more motors and pull wires that control the articulation of the distal end of the introducer. In response to the steering instruction 810, the introducer steering system 812 causes the distal end to bend or articulate in the direction (and in some cases magnitude) as indicated by the steering instruction 810. For instance, steering system may actuate one or more motors to pull or provide additional tension on one or more pull wires to carry out the steering instruction 810.

The techniques introduced above may be implemented for a variety of medical devices or devices where direct and indirect views are possible. A person of skill in the art will understand that the technology described in the context of a video laryngoscope for human patients could be adapted for use with other systems such as laryngoscopes for non-human patients or medical video imaging systems.

Those skilled in the art will recognize that the methods and systems of the present disclosure may be implemented in many manners and as such are not to be limited by the foregoing aspects and examples. In other words, functional elements being performed by a single component or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible.

Functionality may also be, in whole or in part, distributed among multiple components, in manners now known or to become known. Thus, a myriad of software/hardware/firmware combinations are possible in achieving the functions, features, interfaces and preferences described herein. Moreover, the scope of the present disclosure covers manners for carrying out the described features and functions and interfaces, and those variations and modifications that may be made to the hardware or software firmware components described herein as would be understood by those skilled in the art now and hereafter. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A method for steering an introducer with a video laryngoscope, the method comprising:

receiving an image from a camera of a video laryngoscope, the image including a distal end of an introducer and an anatomical structure;

providing the image as an input to a trained machine-learning (ML) model, wherein the ML model is trained to classify images as steering instructions for the introducer, and the trained ML model is trained using a training dataset including a first set of training images pre-classified with a first steering instruction and a second set of training images pre-classified with a second steering instruction;

receiving as output from the trained ML model, a classification of the image;

based on the classification, generating a steering instruction for the introducer; and causing the distal end of the introducer to be steered in accordance with the steering instruction.

2. The method of claim 1, further comprising:

receiving an indication to automatically steer the introducer, wherein generating the steering instruction for the introducer is in response to the indication to automatically steer the introducer.

3. The method of claim 1, wherein the anatomical structure is a trachea or vocal cords.

4. The method of claim 1, the method further comprising:

displaying, at the video laryngoscope, a visual indicator associated with the steering instruction.

5. The method of claim 1, wherein the classification includes the steering instruction and wherein the steering instruction includes a direction and a magnitude for steering the distal end.

6. The method of claim 5, wherein the classification of the image is selected from a finite set of at least four classifications.

7. The method of claim 1, wherein the image is from a video feed of the camera of the video laryngoscope.

8. The method of claim 1, the method further comprising:

determining that the introducer is advancing at a rate of speed, wherein generating the steering instruction for the introducer is based on the rate of speed.

9. A video laryngoscope comprising:

a handle portion;

a display screen coupled to the handle portion;

a blade portion, coupled to the handle portion, configured to be inserted into a mouth of a patient;

a camera, positioned at a distal end of the blade portion, that acquires a video feed while the video laryngoscope is powered on;

a memory storing a trained machine-learning (ML) model; and a processor that operates to:

receive an indication to automatically steer an introducer;

receive an image of the video feed from the camera in real time, the image comprising a single frame of the video feed depicting an introducer portion associated with a distal end of the introducer;

classify, by the trained ML model, the image, wherein the classification includes the steering instruction and the classification is selected from a finite set of at least four classifications;

based on the classification of the image, generate a steering instruction to steer the distal end of the introducer; and send the steering instruction to a steering system of the introducer to bend the distal end of the blind introducer in the steering direction.

10. The system of claim 9, wherein the image is the only input into the trained ML model.

11. The system of claim 9, wherein manual steering of the introducer at the video laryngoscope is prevented while the automatic steering instructions are sent to the introducer.

12. A method for steering a blind introducer via a third-person perspective camera, the method comprising:

receiving a video feed from a camera having a third-person view of a blind introducer, the video feed including a distal end of the blind introducer;

receiving a first image from the video feed of the camera;

classifying, by a trained machine-learning (ML) model, the first image with a first classification;

determining, based on the first classification, a first bending angle for the distal end of the blind introducer;

instructing a steering system of the blind introducer, in real time, to bend the distal end according to the determined first bending angle;

receiving a second image from the video feed of the camera; and classifying, by the trained ML model, the second image with a second classification, in real time.

13. The method of claim 12, wherein the second classification is associated with no action of the distal end of the blind introducer.

14. The method of claim 12, further comprising:

determining, based on the second classification, a second bending angle for the distal end of the blind introducer; and instructing a steering system of the blind introducer, in real time, to bend the distal end according to the determined second bending angle.

15. The method of claim 12, wherein the ML model is trained to classify images as steering instructions for the blind introducer, and the trained ML model is trained using a training dataset including a first set of training images pre-classified with a first steering instruction and a second set of training images pre-classified with a second steering instruction.

16. The method of claim 12, wherein the classification includes a steering instruction including a direction and a magnitude for steering the distal end.

17. The method of claim 12, wherein the first classification and the second classification are selected from a finite set of at least four classifications.

18. The method of claim 12, wherein the camera is part of a video laryngoscope.

19. The method of claim 18, wherein the method is performed by the video laryngoscope.

20. The method of claim 19, wherein the blind introducer is physically coupled to the video laryngoscope.

* * * * *